(12) United States Patent
Jackson

(10) Patent No.: US 6,224,598 B1
(45) Date of Patent: May 1, 2001

(54) BONE SCREW THREADED PLUG CLOSURE WITH CENTRAL SET SCREW

(76) Inventor: Roger P. Jackson, 6600 Indian La., Mission Hills, KS (US) 66208

( * ) Notice: Subject to any disclaimer, the term of this patent is extended or adjusted under 35 U.S.C. 154(b) by 0 days.

(21) Appl. No.: 09/505,763

(22) Filed: Feb. 16, 2000

(51) Int. Cl.[7] .............................. A61B 17/70; A61B 17/86
(52) U.S. Cl. ................................................ 606/61; 606/73
(58) Field of Search .................................. 606/73, 65, 66, 606/61

(56) References Cited

U.S. PATENT DOCUMENTS

| | | |
|---|---|---|
| 4,887,596 | 12/1989 | Sherman . |
| 5,005,562 | 4/1991 | Cotrel . |
| 5,067,955 | 11/1991 | Cotrel . |
| 5,129,388 | 7/1992 | Vignaud et al. . |
| 5,154,719 | 10/1992 | Cotrel . |
| 5,217,497 * | 6/1993 | Mehdian ................................. 606/61 |
| 5,257,993 | 11/1993 | Asher et al. . |
| 5,261,907 | 11/1993 | Vignaud et al. . |
| 5,261,912 | 11/1993 | Frigg . |
| 5,346,493 | 9/1994 | Stahurski et al. . |
| 5,385,583 | 1/1995 | Cotrel . |
| 5,443,467 * | 8/1995 | Biedermann et al. .................. 606/61 |
| 5,487,742 | 1/1996 | Cotrel . |
| 5,496,321 | 3/1996 | Puno et al. . |
| 5,545,165 * | 8/1996 | Biedermann et al. .................. 606/73 |
| 5,562,663 | 10/1996 | Wisnewski et al. . |
| 5,630,817 | 5/1997 | Rokegem et al. . |
| 5,643,260 | 7/1997 | Doherty . |
| 5,697,929 | 12/1997 | Mellinger . |
| 6,059,786 * | 5/2000 | Jackson .................................. 606/73 |
| 6,063,090 * | 5/2000 | Schlapfer ............................... 606/61 |

\* cited by examiner

Primary Examiner—Paul J. Hirsch
(74) Attorney, Agent, or Firm—John C. McMahon

(57) ABSTRACT

A threaded plug closure for an open-ended bone screw has a center bore and is threaded to receive a set screw. The set screw includes a breakaway head and a base which is slotted to permit removal following installation. The base includes an axial point and circumferential ring which engage the center portion of an associated spinal rod. The plug closure and the set screw can be independently installed and the set screw tightened to cooperatively provide capture and locking of the rod or connector in order to secure the rod or connector against translational and rotational movement relative to the bone screw.

9 Claims, 2 Drawing Sheets

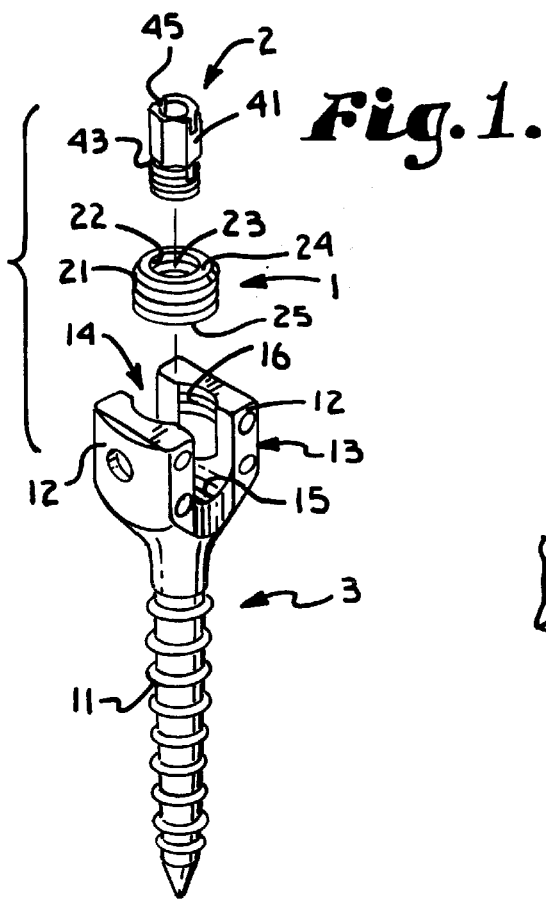
Fig.1.
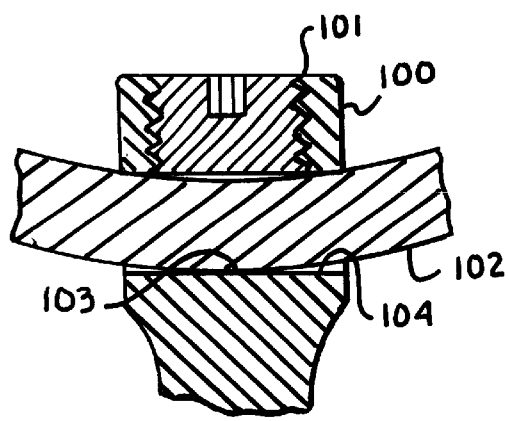
Fig.7.
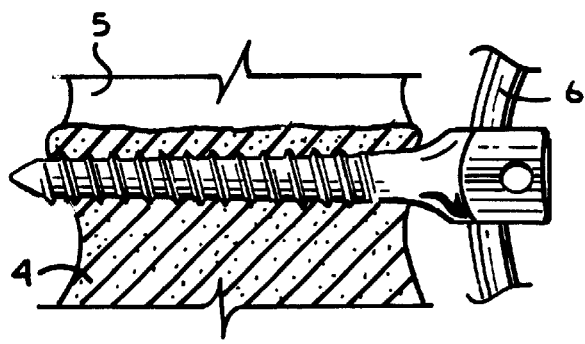
Fig.2.
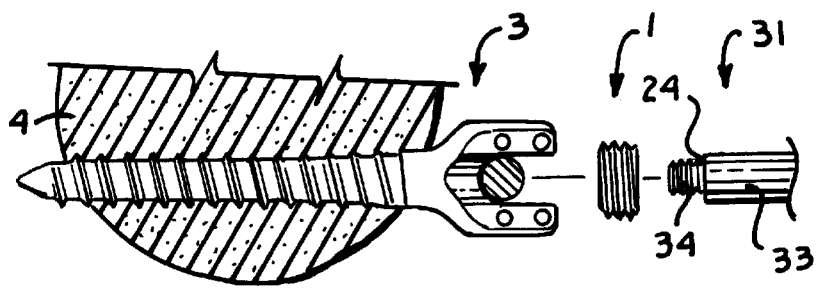
Fig.3.

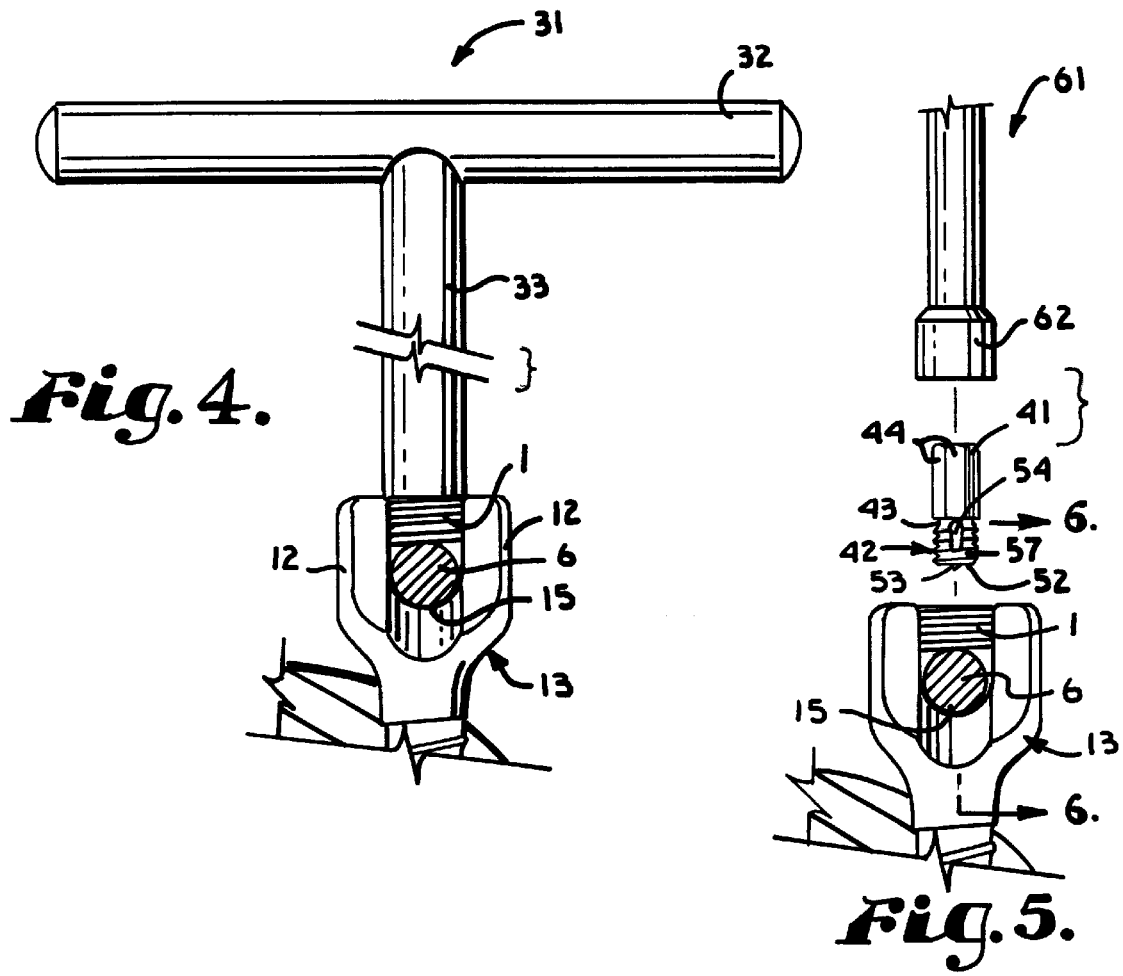
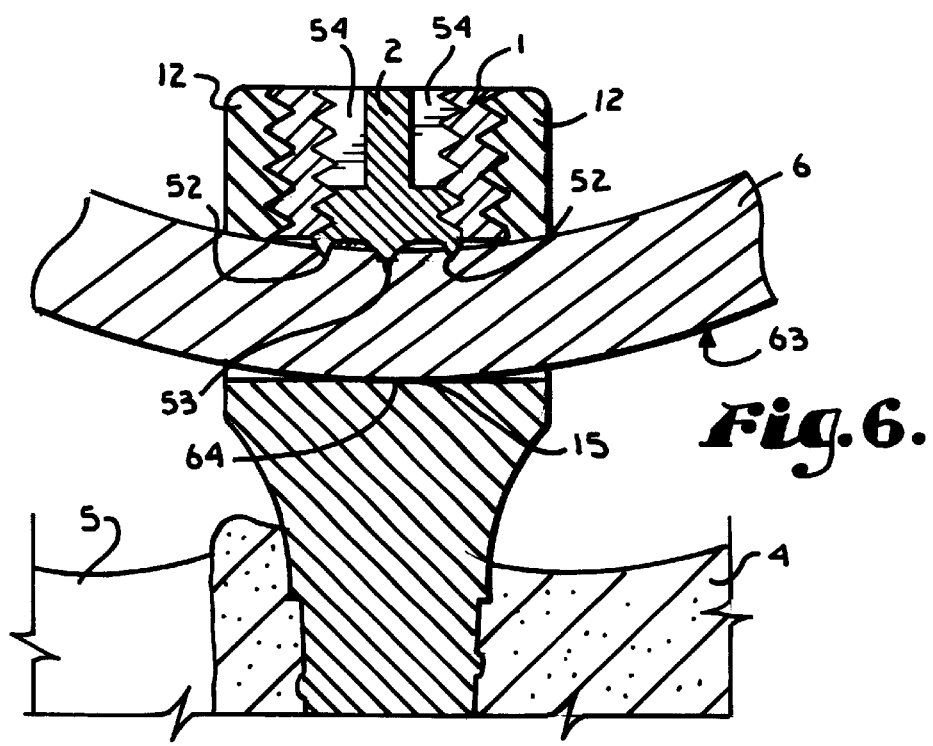

BONE SCREW THREADED PLUG CLOSURE WITH CENTRAL SET SCREW

BACKGROUND OF THE INVENTION

The present invention is broadly directed to a plug closure for a medical implant such as a bone screw. More particularly, it is concerned with an exteriorly threaded plug which further has a threaded center bore that receives a set screw.

Bone screws are often employed in surgically implanted osteosynthesis apparatus, especially for fastening rods and transverse connectors to the spinal vertebrae for the purpose of stabilizing and/or adjusting spinal alignment. While both closed and open-ended types of bone screws are known, open-ended screws are particularly well suited for rod and connector arm installation and adjustment, because the rod does not have to be threaded through a bore, but rather can be laid or urged into an open receiver for the rod.

Such open-ended bone screws include a threaded shank coupled with a pair of upright branches which form a yoke having a U-shaped slot or groove for receiving a rod. Hooks and connectors also sometimes include open ends for receiving rods or the like. The rod is placed in the groove in generally perpendicular relation to the shank, and the open end of the yoke is closed off by a closure device. The closure device includes structure that is tightened against the rod or the like to hold the rod in place against the bottom of the groove. The closure device must hold and firmly secure the rod, in order to prevent rotational or translational movement of the rod relative to the bone screw following installation.

Prior art closure devices have varied in type and one of those types is a simple plug. That is, the interior walls of the branches are threaded and a similarly threaded plug is screwed into the bone screw between the branches to capture and hold the rod in the groove and between the branches. Because the branches must be spaced at least as wide as the rod, the plug must also be at least as wide, if not wider, than the rod. The plug must also not disassemble accidentally from the bone screw during use and the rod must be held securely enough by the plug to prevent rotation and axial relative movement between the rod and bone screw.

In order to perform the functions required of it, the plug should be tightly torqued relative to the bone screw. If the rod were linear, this could be accomplished with some difficulty. However, this is very seldom the case. In particular, the rod is almost always bent at each bone screw in a plane extending from front to rear in the patient in order to correctly position the rod for normal curvature of the back. Because the rod is bent, it does not rest flat against the bottom of the bone screw receiving groove, but tends to be raised one or both opposite ends. After installation, when the back is bent by the patient during activity, the rod will flex slightly about the bone screw. Consequently, even if the plug is torqued to a selected torque (for example, 100 inch pounds is commonly used), the plug may have substantially less or no torque when the rod is flexed, so as to allow the rod to slip. This is because the plug is comparatively wide and rests on the raised portions of the rod. As the rod bends and the raised portions subside, the plug becomes loose.

While a plug is very simple and thus desirable to use, a construction is needed to keep the plug and rod from becoming loose and allowing the rod to move relative to the bone screw, especially when the rod is flexed.

SUMMARY OF THE INVENTION

The present invention overcomes the problems previously described by providing a threaded plug closure for an open-ended bone screw. The plug has a center bore that is threaded to receive a set screw. Preferably, the set screw includes a breakaway head, so as to provide a low profile after insertion, and a base which is slotted to permit removal following installation. The base includes an axial point and circumferential ring which engage and secure against rotation or axial movement an associated spinal rod extending through the bone screw. An annular bottom surface of the plug may also engage the rod laterally with respect to the set screw. The plug closure and the set screw are independently installed and tightened to cooperatively to firmly fix the rod with respect to translational and rotational relationship relative to the bone screw when installation is complete. The set screw is torqued to a preselected torque. Where a break off head set screw is utilized, the head breaks away at the preselected torque.

OBJECTS AND ADVANTAGES OF THE INVENTION

The principal objects of the present invention include: providing a plug closure for an open-ended bone screw or the like having an open rod receiving yoke for use in an osteosynthesis apparatus for securing a rod or other elongate member against rotational and translational movement within the yoke of the bone screw or the like; providing such a plug closure which has a center bore to receive a set screw; providing such a plug closure which includes a central set screw which can be tightened to centrally engage a portion of an associated elongate member which remains seated against the bottom surface within the yoke even though parts of the rod spaced from the engaged portion are spaced away from the bottom surface of the yoke; providing such a plug closure which includes a set screw having a head which breaks off during tightening at a preselected torque after the set screw has been tightened against the rod; providing such a set screw having a base which includes slots extending radially into the base and which can be accessed following installation and break away of the head to efficiently remove the set screw; providing such a plug closure and set screw which can be independently installed and tightened within the yoke of a bone screw to cooperatively engage and secure an associated rod or the like; and providing such an apparatus which is relatively easy to use, inexpensive to produce and particularly well-suited for its intended usage.

Other objects and advantages of this invention will become apparent from the following description taken in conjunction with the accompanying drawings wherein are set forth, by way of illustration and example, certain embodiments of the invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a bone screw having a plug closure with a central set screw in accordance with the present invention.

FIG. 2 is a fragmentary front view of a vertebral body of a patient with an implanted, open ended bone screw having a rod positioned in the yoke of the screw with portions broken away to show detail thereof.

FIG. 3 is a fragmentary top plan view of the vertebral body similar to FIG. 2, showing a plug closure and plug insertion tool prior to assembly, with the head of the tool positioned in alignment with the plug closure preparatory to engagement of the tool with the bore of the closure and the closure with the threaded yoke of the implanted bone screw with portions broken away to show detail thereof.

FIG. 4 is a fragmentary top plan view of a vertebral body similar to FIG. 3, illustrating the plug insertion tool inserting the plug into the threaded bone screw yoke.

FIG. 5 is a fragmentary top plan view of the vertebral body, illustrating a plug closure in the implanted bone screw and a set screw insertion tool aligned with a set screw preparatory to use in inserting the set screw into a receiving threaded bore of the plug closure.

FIG. 6 is a fragmentary front plan view of the vertebral body with the implanted bone screw with the installed plug closure and set screw securing the spinal rod in position in the yoke, especially at and near the center point of the set screw.

FIG. 7 is a cross-sectional view of a prior art bone screw having a closure plug holding a rod in a yoke thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The drawings in FIGS. 1 to 7 illustrate a plug closure, generally designated by the reference numeral 1, in accordance with the present invention used in conjunction with a set screw 2 and an open-ended bone screw 3, which has been implanted by a surgeon into a vertebral body 4 of a human vertebra, having an associated intervertebral disc 5. In the normal human spine, such vertebral bodies 4 are arranged in stacked, spaced relationship, interleaved by the discs 5, which impart a measure of flexibility to the spinal column. Where the vertebrae are improperly aligned, because of congenital deformity, osteoporosis, injury or the like, a series of bone screws 3 may be implanted in various vertebral bodies 4 for coupling with an elongate round or otherwise cross-sectioned rod, transverse connector or the like and in the illustrated embodiment the bodies 4 are coupled to a rod 6 having a uniform circular cross-section. The angle of the rod 6 is then adjusted in order to bring the vertebral bodies 4 into proper alignment, or as close thereto as is possible, normally by bending the rod 6 between front and rear.

The bone screw 3 includes a threaded shank 11 coupled with a pair of opposed upright branches 12 which form a yoke 13. The yoke 13 defines a central slot or channel 14 having a curvate, rod-receiving bottom surface 15. Each yoke branch 12 includes an inner surface 16, a portion of which is threaded in an integrated manner that allows a threaded object of the same diameter and thread to be received in and advanced along the threaded portion of the surface 16.

A plug closure 1, includes a radially outer surface 21 and a threaded central bore 23 having an interior surface 22. The outer surface 21 is threaded for mating engagement with the threads of the yoke inner surface 16. Upper and lower annular plug closure surfaces or rings 24 and 25 are generally planar. Normally the plug upper surface 24 is positioned below or even with the top of the bone screw 3 subsequent to installation to provide a low profile.

An associated plug closure driving tool 31, shown in FIGS. 3 and 4, includes a generally T-shaped handle 32 centrally coupled with and extending perpendicular with respect to an elongate shaft 33. The shaft has a terminus 34 opposite the handle 32 that is threaded for mating engagement with the central bore 23. A shoulder 35 extends radially outward from the terminus 34 whereat the terminus joins to a remainder of the shaft 33.

The set screw 2, includes a head 41 and a base 42, see FIGS. 1 and 5, originally joined together along a breakaway region 43. The outer surface of the head 41 includes a plurality of planar faces 44. A hexagonal configuration of planar faces 44 is depicted in FIG. 1, although those skilled in the art will appreciate that any suitable configuration may be employed. The upper surface of the head 41 includes a pair of notches or drive slots 45 for receiving a flat head driving tool which may be employed in certain applications for starting the set screw 2 into the plug closure 1. As shown in FIG. 1, the head 41 may also include a bore 46, which extends axially toward the breakaway region 43. In other preferred embodiments, the head is of solid construction except for the drive slot 45.

The base 42 has an outer cylindrical shaped surface 51 which is threaded for registry with the threaded central bore 23 of the plug closure 1. As best shown in FIGS. 5 and 6, the threaded base 42 terminates in a sharp edged annular ring 52 that is radially spaced from a central and axially projecting point 53. The base threaded surface 51 and breakaway region 43 include a pair of opposed vertically elongate slots 54 which extend radially inwardly, but do not intersect. The purpose of the slots 54 is to accommodate a removal tool (not shown) and they may be formed by milling or drilling.

Set screw 2 is driven by a hexagonal socket type torque wrench 61 partially shown in FIG. 5. The wrench 61 is similar in construction to the plug closure driving tool 31, except that a terminus 62 thereof is configured as a hexagonal socket for receiving the planar faces 44 of the set screw head 41.

As shown in FIGS. 3–6, the plug closure 1 and set screw 2 are effectively utilized for securing the rod 6 within the bone screw channel 14 against translational or rotational motion. The illustrated rod 6 is bendable by tools well known in the art and is generally circular in cross-section. In the illustrated embodiment the rod 6 is bent so as to be non-linear at the location where the rod 6 is positioned over the rod receiving surface 15. In particular, the rod 6 has a portion 64 that touches the surface 15 at or near the center of the surface 15, but bends outwardly the from the surface 15 on each side of the center. Thus the rod 6 presents a surface 63 which is curved both axially and circumferentially within the bone screw yoke 13. In particular, because of the axial curvature of the rod 6, upon installation the rod 6 rests in the bone screw channel 14 so that only the central portion 64 of the rod surface 63 makes contact with the channel bottom surface 15, while the remainder of the surface 63 within the sides of the bone screw curves away, so as to be in spaced relationship, from the bottom surface 15.

The plug closure 1, set screw 2, rod 6 and associated driving tools 31 and 61 may be constructed of any suitable biocompatible material. Stainless steel and titanium are particularly preferred materials because of their strength and suitability for surgical use and implantation. The rod 6 is generally constructed to include a smooth exterior surface, although a knurled surface may also be employed.

In use, a bone screw 3 is implanted into an area of bone 4, such as, for example, a vertebra of a patient. As shown in FIG. 2, the implanted shank 11 passes into the vertebral body 4 and preferably slightly through the body 4, while the yoke 13 extends outwardly for receiving the elongate rod 6 (or similarly shaped element). The rod 6 is of a size slightly smaller than the bone screw channel 14 and is positioned in the channel 14 in generally perpendicular relationship to the screw shank 11.

A surgeon grasps the handle 32 of a plug closure tool 31, aligns the terminus 34 with a plug closure 1, and rotates the handle in a clockwise direction until the terminus 34 is threaded into the center bore 23 and abuts the shoulder 24. The surgeon, with the rod 6 positioned within the yoke 13, then coaxially aligns the threaded plug closure 1 with the threaded inner surfaces 16 of the yoke 13 of the bone screw 3 and continues rotation of the handle 32 until the closure 1 is threaded into the yoke 13 and is advanced against the rod 6. If the plug 1 is tightened this biases the rod central portion 64 against the bottom surface 15 of the channel 14. Continued rotation of the handle advances the plug closure 1 and the annular lower surface 25 is snugged against the curvate upper surface 63 of the rod 6. The surgeon removes the plug closure driving tool 31 from the center bore 23 by rotating the tool handle 32 counterclockwise.

After the rod 6 is finally adjusted, the surgeon next grasps the set screw socket wrench 61, aligns the terminus 62 with a set screw head 41 and rotates the wrench 61 in a clockwise direction until the set screw base 42 is threaded into the plug closure center bore 23. The wrench 61 is then rotated to advance the set screw 2 until the axial point 53 engages and bites into the rod surface 63. Because of the curvature of the rod 6, the base ring 52 discontinuously engages the rod surface 63 at two opposed points, one on either side of the axial point 53. In this manner, the set screw axial point 53 and base ring 52 cooperatively form a three point anchor at the rod central portion 64 which secures the rod 6 against rotation, axial movement and inadvertent dislodgment of the rod 6 from the bone screw 3. Because the point 53 and ring 52 preferentially cut or penetrate into the surface of the rod 6, the rod 6 is secured better against forces trying to rotate or axially move the rod 6 in comparison to friction acting on other engaging surfaces. The axial point 53 secures the rod against rotational movement within the channel 14, while the engagement of the rod 6 at the two in-line points by the base ring 52 in conjunction with the axial point 53 secures the rod against translational movement. This stable system serves to effectively resist movement of the rod 6 relative to the bone screw 3. It is especially noted that the set screw point 53 engages the rod 6 approximately directly opposite the location where the rod 6 engages the lower yoke surface 15, so that even if outer ends of the rod 6 flex during later use, that this does not loosen set screw 2 and the rod 6 remains securely held against movement.

Further rotation of the wrench 6 produces torque on the set screw head 41 until a preselected torque is reached which causes the head 41 to shear off at the breakaway region 43, as shown in FIG. 6, so that only the base 42 remains threaded in the plug closure center bore 23. After the head 41 is sheared off, the set screw 2 and the plug closure 1 present a clean upper horizontal profile relative to the top of the bone screw 3. The torque at which the head 41 and base 42 shear off is preselected to ensure fixation of the rod 6 within the channel 14 without stripping out the plug closure center bore 23. Penetration of the ring 52 and axial point 53 into the rod 6 stabilizes the set screw 2 and plug closure 1 relative to the rod 6, so that the set screw 2 and plug closure 1 are able to secure the rod 6 to the bone screw 3 even under substantial load.

It is also foreseen that in certain embodiments the plug closure 1 may be pre-loaded into the bone screw 3 prior to implantation of the screw 3 into a patient. In particular, the plug closure 1 may be manually inserted in the threaded yoke 13 of the bone screw 3 prior to implantation in the bone 4 of a patient and rotated just sufficiently to secure the plug 1 in the yoke 13. The bone screw 3 with the coupled plug closure 1 may then be implanted into a bone 4 of a patient. Following insertion of the rod 6 into the bone screw channel 14, the plug closure 1 may then be snugged against the rod 6 preparatory to installation of the set screw 2. It is also foreseen that set screw 2 may be constructed so as not to include breakaway region 43. In that event, the head 41 would remain in place for purposes of removal instead of the slots 54.

In the event that it is necessary to remove or reposition the rod 6, a removal tool may be employed, as described in U.S. patent application Ser. No. 09/177,460 now U.S. Pat. No. 6,059,786 which incorporated herein by reference, to remove the set screw base 42. The terminus 34 of the plug closure driving tool 31 may then be inserted into the threaded central bore 23 of the plug closure 1 and the tool 31 rotated counter clockwise until the plug 1 is either loosened sufficiently to permit adjustment of the rod 6, or removed entirely. The plug 1 is not torqued tightly like the set screw 2 and so is removed comparatively easily.

The plug closure 1 with central set screw 2 of the present invention is described and illustrated in conjunction with a surgically implanted osteosynthesis apparatus anchored by one or more bone screws. However, it is foreseen that the center bored plug closure 1 and set screw 2 of the present invention could be employed in any suitable system.

Shown in FIG. 7 is a conventional bone screw 100 and plug 101 securing a rod 102. The rod 102 is bowed, as is very common in such systems, and, even with the plug 101 tightened, the rod 102 only engages the bottom 103 of the bone screw receiving surface 104 in the middle thereof. If either or both ends of the rod 102 flex during use, the rod 102 pulls away from the plug 101 and becomes loose. This allows the rod 102 to shift axially or rotationally relative to the bone screw 100 and/or the plug 101 to become lose and over time work out of the bone screw 100.

It is to be understood that while certain forms of the present invention have been illustrated and described herein, it is not to be limited to the specific forms or arrangement of parts described and shown.

What is claimed and desired to be secured by Letters Patent is as follows:

1. A plug closure adapted for use in securing a rod member to a bone screw implant; said closure comprising:
   a) a plug having an axis of rotation and a threaded cylindrical shaped outer surface with a maximum outer diameter; said outer diameter being sized and said plug being shaped to be entirely received between a pair of arms of a medical implant during use;
   b) a central bore axially located in and passing entirely through said plug; and
   c) said central bore having an internal threaded surface spaced from said outer surface and sized and shaped to receive a set screw.

2. The plug according to claim 1 wherein said medical implant is a bone screw and in combination with a set screw and said bone screw.

3. The combination according to claim 2 wherein:
   a) said bone screw has a channel sized and shaped to operably receive a rod member and said pair of spaced arms are positioned on opposite sides of said channel; said arms having facing surfaces that are threaded to matingly and threadedly receive the plug therein.

4. The combination according to claim 2 wherein:
 a) said plug closure further includes an upper surface and a lower surface in generally parallel spaced relationship to each other; and
 b) said plug closure being sized so as to be entirely receivable within said bone screw.

5. The plug closure according to claim 1 in combination with a set screw, wherein said set screw includes:
 a) a head having a surface for gripping, rotating and applying torque to said set screw;
 b) a base initially joined to said head and having an outer threaded surface adapted to be threadably received into said plug closure central bore;
 c) said head and said base being joined at a breakaway region for breaking upon application of a preselected torque and separating said head from said base.

6. The plug closure according to claim 5, wherein said set screw base further includes:
 a) a bottom having an axial projecting tip that is coaxially aligned with both said plug closure and said set screw during use;
 b) said tip being sized and shaped to engage and penetrate a rod member during use.

7. A medical implant comprising:
 a) an open bone screw having a threaded shaft adapted to be received in a bone of a patient and an open head with a pair of branches forming a rod receiving yoke therebetween; each of said branches being threaded on facing surfaces thereof and having an inner diameter;
 b) a closure plug having a body with an axis of rotation and an outer threaded surface; said plug having an outer maximum diameter and being sized to be threadedly received in between said branches so said outer maximum diameter of said plug is substantially equal to the inner diameter of said branches; said plug not extending radially outward of said arms inner diameter during use; the threads on each of said branch threaded surfaces and said closure plug being mateable so as to allow said closure plug to be threadably received between said branches during use; said closure plug also having a central threaded bore coaxially located with respect to the axis of rotation of and passing entirely through said plug; and
 c) a set screw having an outer threaded surface that is threadably received in said bore during use so as to be adapted to operably secure a member between said yoke and said plug closure.

8. A medical implant apparatus, comprising:
 a) a first implant having a rod member receiving surface and a threaded aperture above said surface;
 b) a plug closure having a threaded outer surface with a maximum diameter and a central bore passing entirely through said closure; said closure not extending radially outward of said maximum diameter;
 c) said closure outer surface being matingly receivable in said first implant threaded aperture and being sized and shaped to be received entirely within said aperture;
 d) a set screw having a threaded outer set screw surface and being threadably receivable in said closure central threaded bore; and
 e) said set screw having a base including said threaded set screw surface and having a bottom with a coaxial tip positioned to operably engage a rod member during usage.

9. The apparatus according to claim 8 wherein:
 a) said first implant is an open ended bone screw and said rod member is a rod.

\* \* \* \* \*

Disclaimer

6,224,598 B1 — Roger P. Jackson, Mission Hills, KS (US). BONE SCREW THREADED PLUG CLOSURE WITH CENTRAL SET SCREW. Patent dated May 1, 2001. Disclaimer filed August 26, 2014, by the inventor.

Hereby disclaims complete claims 1-4 and 7-9, of said patent.

*(Official Gazette, October 21, 2014)*